United States Patent
Bundsgaard et al.

(10) Patent No.: US 11,826,176 B2
(45) Date of Patent: Nov. 28, 2023

(54) DENTAL FEATURE IDENTIFICATION FOR ASSESSING ORAL HEALTH

(71) Applicant: Adent ApS, Copenhagen K (DK)

(72) Inventors: Richard Bundsgaard, Copenhagen K (DK); Thøger Bundsgaard, Copenhagen K (DK)

(73) Assignee: Adent ApS, Copenhagen K (DK)

( * ) Notice: Subject to any disclaimer, the term of this patent is extended or adjusted under 35 U.S.C. 154(b) by 0 days.

(21) Appl. No.: 17/908,724

(22) PCT Filed: Feb. 26, 2021

(86) PCT No.: PCT/EP2021/054831
§ 371 (c)(1),
(2) Date: Sep. 1, 2022

(87) PCT Pub. No.: WO2021/175713
PCT Pub. Date: Sep. 10, 2021

(65) Prior Publication Data
US 2023/0118333 A1    Apr. 20, 2023

(30) Foreign Application Priority Data

Mar. 3, 2020 (DK) .................................. 202070136

(51) Int. Cl.
*A61B 5/00*        (2006.01)
*G06T 7/10*        (2017.01)
(Continued)

(52) U.S. Cl.
CPC .............. *A61B 5/7275* (2013.01); *A61B 1/24* (2013.01); *A61B 5/0022* (2013.01);
(Continued)

(58) Field of Classification Search
CPC ....... A61B 5/7275; A61B 1/24; A61B 5/0022; A61B 5/0088; A61B 5/4547; A61B 5/4552; A61C 13/34; G06T 7/10; G06V 40/10
See application file for complete search history.

(56) References Cited

U.S. PATENT DOCUMENTS

2016/0038092 A1    2/2016  Golay et al.
2018/0168781 A1*   6/2018  Kopelman ....... A61B 1/000094
(Continued)

OTHER PUBLICATIONS

International Search Report and Written Opinion dated Jun. 11, 2021 from IA PCT/EP2021/054831.
(Continued)

*Primary Examiner* — Nicholas D Lucchesi
(74) *Attorney, Agent, or Firm* — Crockett & Crockett, PC; K. David Crockett, Esq.

(57) ABSTRACT

A computer program and computer-based system for remotely assessing oral health of a person by obtaining at least one digital image (1) of the person's oral cavity and additional non-image data (2) comprising anamnestic information about the person (30). The digital images (1) are segmented using statistical image segmentation algorithms (101,102) to extract visible segments (3), which are further processed to predict any invisible segments (6). The resulting segments are processed by a statistical object detection algorithm (104) using the non-image data (2) as further input to identify dental features (7), which are filtered to select only risk-related dental features (8) using a risk database (9) and mapped to respective tooth regions (11) or oral cavity regions (12) in an Oral Risk Atlas (10).

15 Claims, 5 Drawing Sheets

(51) Int. Cl.
*G06V 40/10* (2022.01)
*A61B 1/24* (2006.01)
*A61C 13/34* (2006.01)

(52) U.S. Cl.
CPC .......... *A61B 5/0088* (2013.01); *A61B 5/4547* (2013.01); *A61B 5/4552* (2013.01); *A61B 5/6898* (2013.01); *A61B 5/7267* (2013.01); *A61B 5/743* (2013.01); *A61B 5/7475* (2013.01); *A61C 13/34* (2013.01); *G06T 7/10* (2017.01); *G06V 40/10* (2022.01); *G06T 2207/10024* (2013.01); *G06T 2207/20081* (2013.01); *G06T 2207/30036* (2013.01)

(56) References Cited

U.S. PATENT DOCUMENTS

2018/0249913 A1* 9/2018 Seibel .............. A61B 1/000094
2019/0333627 A1* 10/2019 Johnson .................. G06N 3/02
2019/0340760 A1 11/2019 Swank et al.

OTHER PUBLICATIONS

Chen, et al., A Deep Learning Approach to Automatic Teeth Detection and Numbering Based on Object Detection in Dental Periapical Films, Scientific Reports, vol. 9, No. 1, Mar. 7, 2019, pp. 2-6.

Cui, et al., ToothNet: Automatic Tooth Instance Segmentation and Identification From Cone Beam CT Images, 2019 IEEE/CVF Conference on Computer Vision and Pattern Recognition (CVPR), IEEE, Jun. 15, 2019, pp. 6361-6370.

Rana, et al., Automated Segmentation of Gingival Diseases from Oral Images, 2017 IEEE Healthcare Innovations and Point of Care Technologies (HI-POCT), IEEE, Nov. 6, 2017, pp. 144-147.

Anantharaman, et al., Utilizing Mask R-CNN for Detection and Segmentation of Oral Diseases, 2018 IEEE International Conference on Bioinformatics and Biomedicine (BIBM), IEEE, Dec. 3, 2018, pp. 2197-2204.

* cited by examiner

DENTAL FEATURE IDENTIFICATION FOR ASSESSING ORAL HEALTH

TECHNICAL FIELD

The present disclosure relates generally to the field of oral health, and more particularly to a method for processing digital images and non-image data, such as text input, obtained using a mobile device, to identify dental features.

BACKGROUND

Oral health assessment is crucial for early intervention against and preventive treatment of oral health problems. However, many people do not receive proper oral health assessment, for several reasons. For example, they may live in rural areas far from a dental clinic and may, hence, not have access to oral health assessment, or they may not have the economic means to consult with a dental professional, let alone to pay for a potential treatment. Further, many people may be disinclined to spend time and money on an initial oral health assessment or on regular dental checkups if they are not experiencing any apparent oral health problem, despite the fact that, sometimes, people may unknowingly have symptoms of compromised oral health or unknowingly be at risk of developing an oral health problem. In other cases, people may be experiencing a certain oral health problem or symptoms of an oral disease but may decide to wait before consulting with a professional, hoping that the problem or symptoms will go away.

All these example scenarios are problematic since early and proper oral health assessment allows for early intervention and preventive treatment, thus preventing or reducing the occurrence or progress of many oral problems and diseases.

Systems for remote oral health assessment, often referred to as teledentistry, exist. These systems typically provide real-time and offline dental care such as diagnosis, treatment planning, consultation, and follow-up through electronic transmission of clinical data among patients and dental professionals, e.g. using smartphones or other mobile devices. Some known remote oral health assessment systems involve transmission of e.g. dental images from the patient. For example, the patient may use the front camera of his/her smartphone for capturing a dental image and may transmit the captured image via e.g. a web-based application on the smartphone for remote clinical assessment. However, these transmitted images are most commonly assessed visually by a dental professional, with or without taking into account additional clinical data regarding the patient's clinical history from a local or remote database. This process is not only costly but also requires a lot of time to get results, which may cause serious health issues in case a medical condition is recognized too late.

In similar fashion, early detection of oral health related medical conditions and providing actionable, easy-to-follow, personalized advice regarding such a condition can not only prevent the escalation of such conditions but save the patient or an insurance provider of the patient a lot of money otherwise spent on expensive treatments.

Accordingly, there is a need for technologies that can provide patients, dental professionals and insurance providers with a fast, precise, remote assessment of current and future risk levels of a patient based on the current state of the patient's oral cavity and additional anamnestic information that the patients can provide using existing tools, such as a mobile device that is connected to the Internet and comprises an input interface (e.g. touchscreen) and a camera, without requiring medical expertise or training.

There further exists a need for an efficient and reliable processing method which is capable of assessing dental risks based on dental features identified by processing both image and non-image input provided by an untrained user on a low-cost mobile device and which can provide, as a result, a visualized map of dental features or assessments of dental risks related to the oral health of the patient.

There further exists a need for systems and methods capable of visualizing such a map of dental features or assessments of dental risks in a way that is customizable based on an end user such as a patient, dental professional or insurance provider, and can support a decision-making process for each end user individually.

SUMMARY

It is an object to provide a method and corresponding computer program product and computer-based system that fulfills these needs and thereby overcomes or at least reduces the problems mentioned above. The foregoing and other objects are achieved by the features of the independent claims. Further implementation forms are apparent from the dependent claims, the description, and the figures.

According to a first aspect, there is provided a computer program comprising instructions which, when the program is executed by a computer, cause the computer to:

obtain at least one digital image of the person's oral cavity using a digital camera;

obtain non-image data associated with the person, the non-image data comprising anamnestic information about the person;

process the at least one digital image or a representation thereof using a first statistical image segmentation algorithm trained to identify at least one visible segment, the visible segment being one of a tooth segment or an oral cavity segment, wherein each tooth segment relates to a distinct tooth and its related area within the oral cavity and each oral cavity segment relates to a distinct non-tooth-related area within the oral cavity;

process the at least one visible segment using a statistical algorithm trained to predict any invisible segments based on visible segments, each invisible segment relating to an area within the oral cavity that is not visible on any of the at least one digital image; and process the at least one visible segment and the at least one invisible segment using a statistical object detection algorithm trained to identify dental features linked to the respective segments, wherein the statistical object detection algorithm uses the non-image data as input regarding what dental features to look for.

The solution presented in the first aspect improves identification of dental features by supplementing visible segment data with invisible segment data, and further taking into account non-image data input to for the accurate and efficient identification of features. This ultimately provides end users including patients, dental professionals and insurance providers alike with quick and affordable access to high quality, detailed, remote assessment be enabling assessment on the potential oral health risks of a patient.

The assessment is based on the current state of the patient's oral cavity and further inputs (e.g. text-based input via an application) thereby ensuring up-to-date and precise information input. The images provided are segmented and analyzed by various statistical algorithms to identify e.g. tooth segments and regions and the results can be mapped onto an existing identification framework, thereby ensuring both preciseness and comprehensibility of the presented information.

In a possible implementation form of the first aspect, the computer program comprises further instructions which, when the program is executed by a computer, cause the computer to:

select risk-related dental features from the identified dental features using a risk database that defines logical relationships between dental features and their related oral health risks;

generate an Oral Risk Atlas by mapping risk-related dental features linked to any tooth segment to a respective tooth region according to a predefined dental notation framework, mapping risk-related dental features linked to any oral cavity segment to a respective oral cavity region according to a predefined oral cavity surface identification framework, and mapping risk-related dental features linked to any invisible segment to a respective tooth region or oral cavity region according the predefined dental notation framework and the oral cavity surface identification framework; and display the Oral Risk Atlas on a user interface.

Mapping dental features to respective regions of the oral cavity of the patient further supports decision-making for end users. The Oral Risk Atlas can be a useful tool for dental professionals for pre-screening new patients, for providing an additional "second opinion" before a planned surgery or intervention for existing patients, as well as an effective and easy-to-use interface for communicating risks and priorities for patients regarding possible treatments or interventions or the lack thereof (e.g. getting a crown now or a bridge now and a crown in five years).

The method thus allows for a standardized, remote and timely feedback to the user and their dental professionals or even their insurance providers to assess oral health risks and to pinpoint regions of the oral cavity that may require professional attention for reducing such risks.

In a possible implementation form of the first aspect, the computer program comprises further instructions which, when the program is executed by a computer, cause the computer to:

process the at least one tooth segment using a second statistical image segmentation algorithm trained to identify at least one tooth surface segment and at least one periodontal surface segment, each tooth surface segment relating to a distinct surface of a distinct tooth within the oral cavity and each periodontal surface segment relating to a structure surrounding or supporting a distinct tooth within the oral cavity;

process the at least one tooth surface segment and at least one periodontal surface segment using a statistical algorithm trained to predict any invisible surface segments, each invisible surface segment relating to a distinct surface of distinct tooth or a structure surrounding or supporting a distinct tooth within the oral cavity that is not visible on any of the at least one digital image;

identify dental features by processing the at least one tooth surface segment, periodontal surface segment and invisible surface segment using the statistical object detection algorithm; and select risk-related dental features from the identified dental features using the risk database;

wherein generating the Oral Risk Atlas further comprises mapping the risk-related dental features linked to the tooth surface segments to a respective tooth surface region according to a predefined dental surface identification framework, mapping the risk-related dental features linked to the periodontal surface segments to a respective periodontal surface region according to a predefined dental surface identification framework, and mapping the risk-related dental features linked to the invisible surface segments to a respective tooth surface region or periodontal surface region according to the predefined dental surface identification framework.

In a possible implementation form of the first aspect, the computer program comprises further instructions which, when the program is executed by a computer, cause the computer to: process the non-image data to extract further risk-related dental features linked to any one of the tooth region, oral cavity region, tooth surface region or periodontal surface region; wherein generating the Oral Risk Atlas further comprises mapping the further risk-related dental features to the respective regions.

By providing a solution that assesses and processes image and non-image data to extract further features linked to certain teeth regions, oral cavity regions, tooth surface regions or periodontal surface regions, the users can accurately identify any problematic areas and can display these to the user in an easily understandable manner, making both the diagnosis of a problem easier and the usability better.

In a possible implementation form of the first aspect the computer program comprises further instructions which, when the program is executed by a computer, cause the computer to determine a dental risk assessment for each tooth region, oral cavity region, tooth surface region and periodontal surface region associated with an identified visible segment using a statistical risk assessment algorithm trained to predict dental risk assessments based on risk-related dental features determined from the respective visible segments; wherein generating the Oral Risk Atlas further comprises mapping the dental risk assessments to the Oral Risk Atlas.

In a possible implementation form of the first aspect the computer program comprises further instructions which, when the program is executed by a computer, cause the computer to determining a dental risk assessment for each tooth region, oral cavity region, tooth surface region and periodontal surface region associated with a predicted invisible segment using a statistical risk prediction algorithm trained to predict dental risk assessments based on risk-related dental features determined from visible segments adjacent to a respective invisible segment; wherein generating the Oral Risk Atlas further comprises mapping the dental risk assessments to the Oral Risk Atlas.

In a possible implementation form of the first aspect the computer program comprises further instructions which, when the program is executed by a computer, cause the computer to determine each dental risk assessment by calculating a dental risk score for each tooth region, oral cavity region, tooth surface region and periodontal surface region as a percentage value (ranging from 1 to 100%) or a discrete value (ranging from 1 to 5); wherein generating the Oral Risk Atlas further comprises mapping the dental risk scores to the Oral Risk Atlas.

In an embodiment the dental risk scores are determined as a percentage value ranging from 1 to 100%, or a discrete value ranging from e.g. 1 to 5.

In an embodiment generating the Oral Risk Atlas further comprises visualizing each percentage value or discrete value in the Oral Risk Atlas using predefined color scheme.

By providing a solution that also presents the relevant data in an easily understandable and standardized way, the users can ensure that the chance of mistakes, misdiagnosis or misunderstanding is reduced.

In a possible implementation form of the first aspect the computer program comprises further instructions which, when the program is executed by a computer, cause the computer to calculate an aggregate dental risk score based on aggregating the dental risk scores for each tooth region, oral cavity region, tooth surface region and periodontal surface region.

In a possible implementation form of the first aspect the computer program comprises further instructions which, when the program is executed by a computer, cause the computer to determine a number of dental risk types based on the risk-related dental features; wherein generating the Oral Risk Atlas further comprises mapping the number of dental risk types to the Oral Risk Atlas. In a possible embodiment, the dental risk types are one of tooth-structural, periodontal-structural or mucosa-based risk-related dental features. In a possible embodiment, the dental risk types are displayed in the Oral Risk Atlas using a predefined geometrical shape for each dental risk type.

By providing a solution that also presents the relevant data in an easily understandable and standardized way, the users can ensure that the chance of mistakes, misdiagnosis or misunderstanding is reduced.

In a possible implementation form of the first aspect at least one of the statistical risk assessment algorithm or the statistical risk prediction algorithm further uses static syntax analysis implemented as iteration over a number of surface regions impacted by a dental feature, each surface region contributing to a higher dental risk score; and predefined conditions on compound contributions to the determined dental risk score.

In a possible implementation form of the first aspect at least one of the statistical risk scoring algorithm or the statistical risk prediction algorithm is further supplemented with syntax analyses aggregating a risk of specific treatments with a cost of the treatment type.

In a possible implementation form of the first aspect at least one of the statistical risk scoring algorithm or the statistical risk prediction algorithm uses a classical linear regression model, an ordinal-data-based statistical algorithm, or neural networks supplemented with syntax analyses of predefined conditions, optionally further supplemented by manual input from a dental professional or querying a dental knowledge database.

In a possible implementation form of the first aspect the computer program comprises further instructions which, when the program is executed by a computer, cause the computer to determine dental risk mitigation assessments comprising possible actions to take for the person based on the risk-related dental features, the further risk-related dental features, the dental risk scores or the aggregate dental risk score, the possible actions comprising at least one of
  home care actions related to following a dental routine or customized dental plan (such as prompts to more frequent flossing, mouth rinse),
  risk-related treatments, or
  prompts to visit a dental professional;
  wherein generating the Oral Risk Atlas further comprises mapping potential gains of the possible actions to the Oral Risk Atlas.

In a possible implementation form of the first aspect at least one of the first or second statistical image segmentation algorithms further uses landmark detection based on landmarks or focal points, supplemented with spatial or vector analyses of orthodontic features, such as the orientation of each tooth and the relation between adjacent and other teeth.

In a possible implementation form of the first aspect at least one of the statistical image segmentation algorithms uses neural networks (e.g. MaskRCNN, YOLO, CNN) based on annotations using an annotation type of at least one of boxes, polygons, or masks.

In a possible implementation form of the first aspect the computer program comprises further instructions which, when the program is executed by a computer, cause the computer to obtain additional non-image data by extracting from a dental journal or dental medical history of the person.

In a possible implementation form of the first aspect generating the Oral Risk Atlas comprises at least one of
  mapping the risk-related dental features or dental risk assessments to respective regions using a matrix scheme;
  mapping the risk-related dental features or dental risk assessments to respective regions based on a 2D or 3D oral cavity model, the oral cavity model being generated using a standardized dental model or a dental model of the person.

In a possible implementation form of the first aspect the computer program comprises further instructions which, when the program is executed by a computer, cause the computer to: provide a dental risk analysis application on a network-accessible computer; and call the dental risk analysis application through the network using a client device.

In a possible implementation form of the first aspect the digital image is at least one of an intraoral or extraoral high resolution color photograph, preferably in the RGB or RGBA color space, obtained through the dental risk analysis application by prompting the person to take a photograph with a digital camera of a client device of one or more areas of the oral cavity of the person.

In a possible implementation form of the first aspect the non-image data is obtained, in the form of at least one of a text input, spoken input or input by selection of selecting at least one of several presented answers, through the dental risk analysis application by performing a dialogue with the person through a user interface of a client device.

In a possible implementation form of the first aspect, risk-related dental features and/or dental risk assessments are filtered before mapping onto the Oral Risk Atlas, wherein the filtering may be based on sensitivity of information or comprehensibility of presented terms.

According to a second aspect, there is provided a computer-based system, the system comprising:
  a digital camera configured to obtain a digital image of an oral cavity of the person;
  an input device configured to obtain non-image data associated with the person, the non-image data comprising anamnestic information about the person;
  a computer-readable storage medium comprising a computer program according to any one of the possible implementation forms of the first aspect;
  one or more processors operable to execute the computer program; and
  a user interface configured to display an Oral Risk Atlas generated by the computer program.

In a possible implementation form of the second aspect, the system comprises a client device comprising at least the digital camera, the input device and the user interface; and a server device in data connection with the client device, the server device comprising at least the computer-readable storage medium and the one or more processors.

These and other aspects will be apparent from and the embodiment(s) described below.

BRIEF DESCRIPTION OF THE DRAWINGS

In the following detailed portion of the present disclosure, the aspects, embodiments, and implementations will be explained in more detail with reference to the example embodiments shown in the drawings, in which.

DETAILED DESCRIPTION

Figure 1:
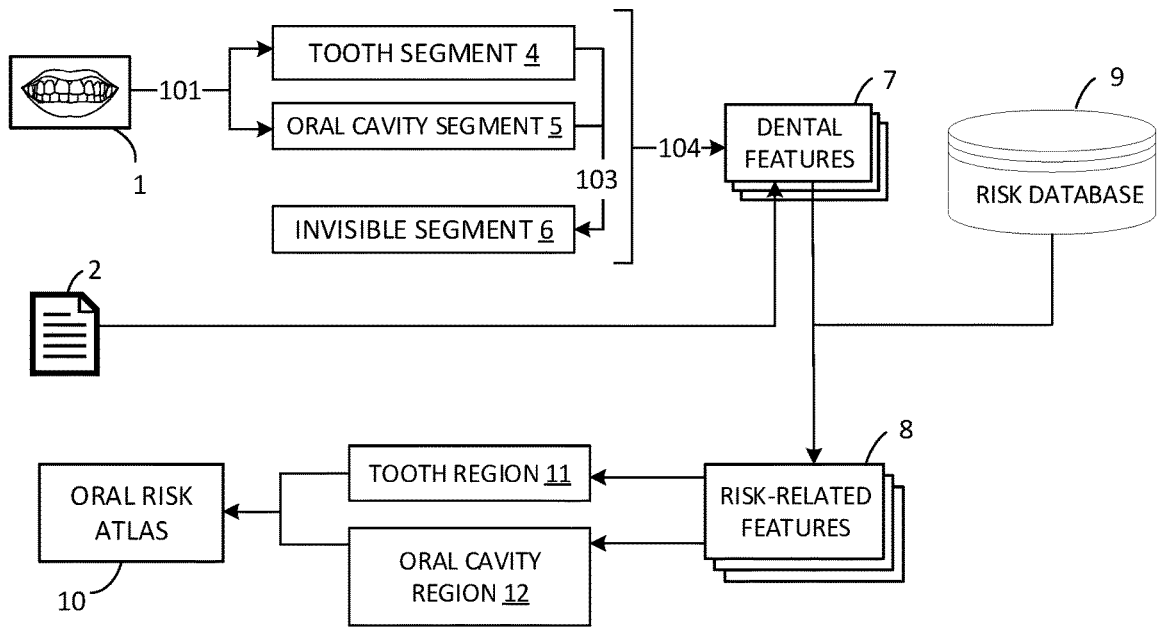
FIG. 1 shows a flow diagram of a method for generating an Oral Risk Atlas in accordance with the first aspect, using a system in accordance with the third aspect.
Figure 9:
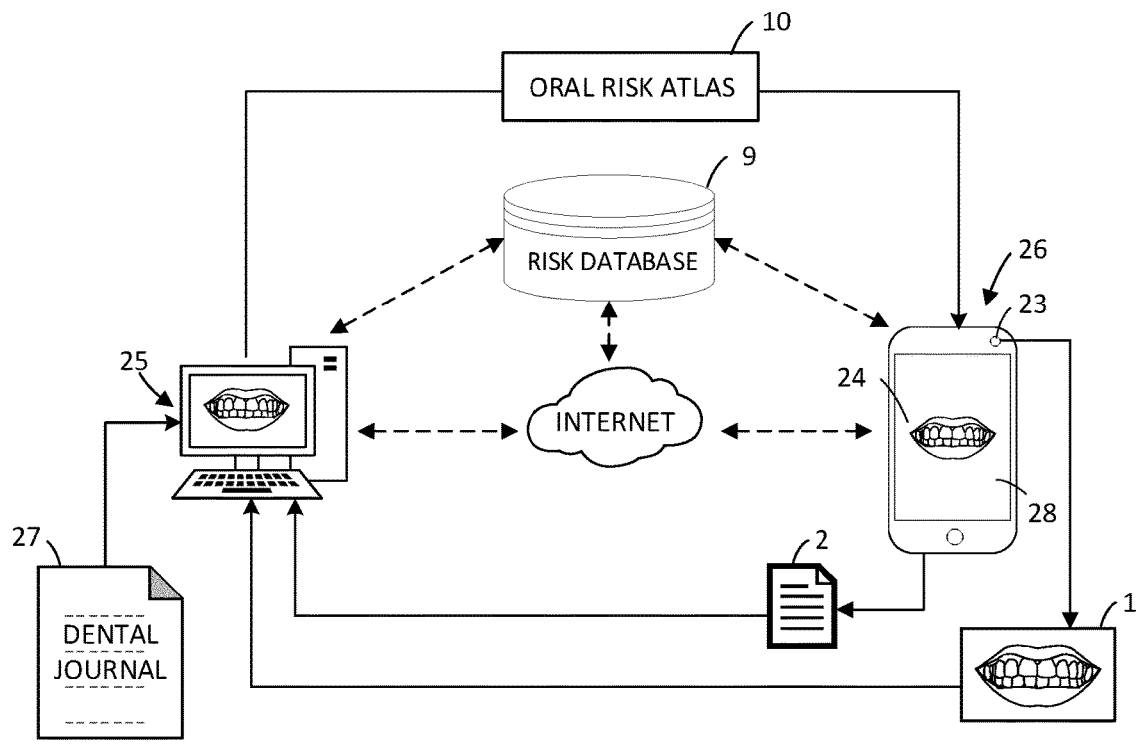
FIG. 9 is a block diagram of a system for assessing oral health of a person in accordance with a possible implementation form of the second aspect.

FIG. 1 shows a flow diagram of a method for assessing oral health of a person in accordance with the present disclosure, implemented as a computer program product encoded on a computer-readable storage medium of a computer-based system such as for example the system shown on FIG. 9.

In an initial step, at least one digital image 1 of the oral cavity of a person is obtained using a digital camera 23. Herein, "oral cavity" may refer to e.g. lips, hard palate, soft palate, retromolar trigone (area behind the wisdom teeth), tongue, gingiva (gums), buccal mucosa, the floor of the mouth under the tongue, and/or teeth.

The person may capture the digital image(s) 1 with a digital camera 23 of a mobile device or any suitable camera device (such as a small intraoral camera used by dental professionals) and/or may add existing images from a gallery available e.g. on or via a mobile device that were taken with the digital camera 23 beforehand. The obtained digital image(s) 1 may be both an intraoral or extraoral high resolution color photograph(s), preferably in the RGB or RGBA color space.

For providing the at least one digital image 1, the person may be prompted to select a particular view/pose annotation describing the view/pose of the images, e.g. closed mouth view, bite view, bottom/lower arch view, upper arch view, bottom/lower lip view, upper lip view, closed bite anterior view, open bite anterior view, closed bite buccal view, open bite buccal view, roof of mouth view, floor of mouth view, side of mouth view, or frontal view, and may be guided to capture an image in the selected particular view/pose. In an embodiment the person may be required to provide at least one image for each of a set of predefined priority views, such as a 'frontal view with closed bite', a 'bottom lip pulled down, exposing teeth in lower mouth and the inner bottom lip' and 'top lip pulled up, exposing teeth in top mouth and the inner top lip'.

In an embodiment, the person whose oral cavity is captured by the digital image 1 is the same person as the person operating the mobile device for obtaining the one or more digital images 1. In another embodiment, the person operating the mobile device is not the same person as the person whose oral cavity is captured on image. This may, for example, be the case when the person whose oral cavity is captured on image is a child or other person requiring help, e.g. from a parent or other family member, for capturing the one or more images of an area of his/her oral cavity.

In addition to the above described digital image 1, non-image data 2 associated with the same person is also obtained. The non-image data 2 comprises anamnestic information about the person, wherein "anamnestic information" may refer to any type of information regarding the patient's medical history as well as any current symptoms (see described below in detail).

Herein, the order of steps does not correspond to a strict order of execution—obtaining the non-image data 2 can happen in the same time, before and/or after obtaining the digital image(s) 1.

In an embodiment the non-image data 2 comprises self-reported user input given by the person via e.g. a touch-screen interface of a device. In an embodiment the non-image data 2 may be obtained in the form of a dialogue, where the person answers an automatically generated or predefined sequence of questions and the answers are recorded on the device. In an embodiment the questions may be received, and the answers may be given in the form of a text input, spoken input or input by selection of selecting at least one of several presented answers in the form of a checklist, a slider bar, a visual representation, and/or free text. In an embodiment, a 3D representation of an oral cavity may be presented to the person for indicating in the representation an area corresponding to the area of the user's own oral cavity associated with an oral health problem. The area may e.g. be a specific tooth. The person's answers may be finite answers. For example, the person may select one or more suggestions from a checklist.

In an embodiment the sequence of questions to the person may comprise questions relating to past and present lifestyle or behavioral data (such as tobacco use, diet, sugar intake, and oral hygiene habits such as brushing), known health or medical conditions (such as diabetes), symptoms, symptom triggers, and/or temporal contextual variables such as urgency. The questions may further relate to prepositions to oral risk, such as a person indicating a high mineralization of their spit, which in turn can lead to accelerated development of plaque/tartar.

In an embodiment the symptoms may be symptoms of at least one of gingivitis, periodontitis, dental caries, abrasion of tooth, bruxism, cold sore, erosion of teeth, fluorosis, herpes labialis, herpes zoster, or herpes infection.

In an embodiment the obtained non-image data 2 further comprises information regarding any teeth to omit from the oral health assessment (such as a missing tooth) and/or information regarding dental features (such as fillings) of existing teeth.

In an embodiment the obtained non-image data 2 further comprises information extracted from a dental journal 27 or dental medical history of the person, the dental journal 27 or dental medical history being provided by the person or being accessed from a database either remotely via a computer network or locally from a workstation of a dental professional.

In a preferred embodiment, the person is presented with a text-based dialogue through a user interface 24 on a display of a client device 26, the dialogue comprising a sequence of questions arranged to guide the person through a process of combined input of both non-image data 2 and digital image(s) 1 in one flow.

Once obtained, both the non-image data 2 and the digital image(s) are processed using a dedicated arrangement of statistical algorithms.

In an embodiment the at least one digital image 1 and the non-image data 2 are processed locally, e.g. on a mobile device, using at least one processor of the mobile device.

In another embodiment the at least one digital image 1 and the non-image data 2 are transmitted, using a computer network, to a server device 25 as shown in FIG. 9, and processed remotely on the server device 25.

In particular, the at least one digital image 1 is processed using a first statistical image segmentation algorithm 101 trained to identify at least one visible segment 3. Each visible segment 3 may represent a tooth segment 4 that relates to a distinct tooth and its related area within the oral cavity and/or an oral cavity segment 5 that relates to a distinct non-tooth-related area within the oral cavity.

Herein, the non-tooth-related area may represent at least one of the gums, mucosa roof/floor of mouth, inner cheeks, tongue, or lips of a person.

In a next step the at least one visible segment 3 (tooth segment 4 or oral cavity segment 5) is further processed using a statistical algorithm 103 trained to predict any invisible segments 6 based on visible segments 3. Herein, each invisible segment 6 relates to an area within the oral cavity that is not visible on any of the at least one digital image 1.

In a next step the visible segment(s) 3 and invisible segment(s) 6 are further processed using a statistical object detection algorithm 104 trained to identify dental features 7 linked to the respective visible and/or invisible segments. Herein, the dental features may represent a wide range of oral health related findings such as fillings or missing teeth; presence of plaque; caries; pigmentation; color of the gums, lips or cheeks; presence of spit bubbles; etc.

In a preferred embodiment the statistical object detection algorithm 104 uses the non-image data 2 as additional input indicating what dental features 7 to look for in the derivative segments of the digital image(s) 1.

In a next step, from the dental features 7 identified in the previous step, the risk-related dental features 8 are selected using a risk database 9 that defines logical relationships between dental features 7 and their related oral health risks. Herein, the fact that a dental feature 7 is selected as a risk-related dental feature 8 means that it is linked in some way to a certain risk regarding the oral health of the person. For example, detected "spit bubbles" may indicate a "moist mouth" of a person which is the inverse of a "dry mouth", the latter being a significant risk indication for developing a series of oral health issues such as increased risk of cavities; whereas "presence of plaque" or "redness of the gums" may directly indicate different oral health risks. Both types of these dental features 7 may be selected as risk-related dental features 8. An example on the other hand for a feature not being linked to a noticeable oral health risk is e.g. "light reflection from camera flash", which would be thus excluded from the risk-related dental features 8.

In a possible and practical embodiment such a risk database 9 inter-relates all dental features 7 with a "probability score" and a "severity score" related to an oral health risk, where the oral health risk typically falls into one of the following categories:

a) The risk of a disorder (specified on type),
b) The risk of a treatment (specified on type), or
c) A more "abstract" risk of getting poorer oral health in an accelerated time period (this should be seen in light of the two above, which could represent two specific edge cases of "disorder" and "treatment", whereas much risk on health is "just" related to a person not having as good health as they could/should/wished to have).

The risk database 9 may be located and accessed from the same (mobile) device used to obtain the digital image 1 and the non-image data 2, or may also be located remotely, e.g. on a server device 25 as illustrated in FIG. 9, and accessed through a computer network by a client device 26.

In a following step, the selected risk-related dental features 8 are mapped to respective tooth or oral cavity regions for generating an Oral Risk Atlas 10.

In particular, risk-related dental features 8 linked to tooth segments 4 may be mapped to respective tooth regions 11 according to a predefined dental notation framework, such as a Palmer, Universal, FDI, or any similar tooth numbering framework.

On the other hand, risk-related dental features 8 linked to oral cavity segments 5 may be mapped to respective oral cavity regions 12 according to a predefined oral cavity surface identification framework designed to differentiate between different surfaces of the oral cavity, such as surfaces of the tongue, surfaces of the lips, or surfaces of the mucosa being a superset of gums, tongue, lips, etc.

Finally, risk-related dental features 8 linked to invisible segments 6 are mapped to respective tooth regions 11 or oral cavity regions 12 according to a predefined dental notation framework and oral cavity surface identification framework as described above.

In a final step, the generated Oral Risk Atlas 10 is displayed on a user interface 24, which user interface 24 may be part of a mobile device used to obtain the digital image(s) 1 and the non-image data 2.

Similarly as described above with respect to processing the at least one digital image(s) 1 and the non-image data 2, in an embodiment the Oral Risk Atlas 10 can be generated locally on a client device 26 using at least one processor of the client device 26.

Similarly, in another possible embodiment the Oral Risk Atlas 10 can also be generated on a remote server device 25 using on the extracted data (dental features 7, and in particular risk-related dental features 8) from the digital image(s) 1 and the non-image data 2 using the above described statistical algorithms, which extracted data may already all be on the server device 25 or can be transmitted thereon using a computer network as shown in FIG. 9. The Oral Risk Atlas 10 can then be transmitted for displaying to the person on a user interface 24 of the mobile device.

Figure 2:
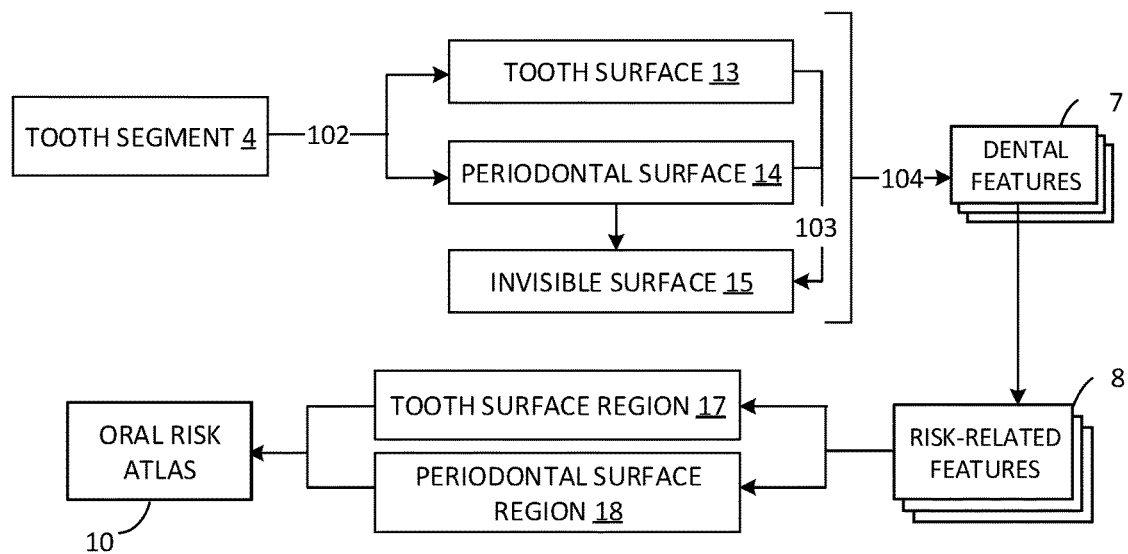
FIG. 2 shows a flow diagram of processing tooth segments using a statistical image segmentation algorithm in accordance with a further implementation form of the first aspect.

FIG. 2 shows a flow diagram of processing tooth segments 4 using a second statistical image segmentation algorithm 102 in accordance with the present disclosure. In this implementation, features that are the same or similar to corresponding features previously described or shown herein are denoted by the same reference numeral as previously used for simplicity.

In particular, as shown in the figure, the method according to the present disclosure can further comprise processing the at least one tooth segment 4 using a second statistical image segmentation algorithm 102 trained to identify at least one tooth surface segment 13 and at least one periodontal surface segment 14. Herein, each tooth surface segment 13 relates to a distinct surface of a distinct tooth within the oral cavity, and each periodontal surface segment 14 relates to a structure surrounding or supporting a distinct tooth within the oral cavity.

In a next step, the at least one tooth surface segment 13 and at least one periodontal surface segment 14 is processed using a statistical algorithm 103 trained to predict any invisible surface segments 15, wherein each invisible surface segment 15 relates to a distinct surface of distinct tooth or a structure surrounding or supporting a distinct tooth within the oral cavity that is not visible on any of the at least one digital image 1.

In a following step, additional dental features 7 (in addition to dental features 7 described above) are identified by processing the at least one tooth surface segment 13, periodontal surface segment 14 and invisible surface segment 15 using the above described statistical object detection algorithm 104, and then, similarly as described above, additional risk-related dental features 8 are selected from the identified dental features 7 using the risk database 9.

In a following step, the risk-related dental features 8 linked to the tooth surface segments 13 are mapped to respective tooth surface regions 17 according to the predefined dental surface identification framework; the risk-related dental features 9 linked to the periodontal surface segments 14 are mapped to respective periodontal surface regions 18 according to the predefined dental surface identification framework; and the risk-related dental features 8 linked to the invisible surface segments 15 are mapped to respective tooth surface regions 17 or periodontal surface regions 18 according to the predefined dental surface identification framework.

Herein, a dental surface identification framework may refer to any existing dental surface model, such as a 5-surface model, 6-surface model, 7-surface model, 8-surface model, or similar, further referring to models that include periodontal surface models such as a 3-surface gum model or 4-surface gum model.

In a final step, as described above with respect to FIG. 1, the generated Oral Risk Atlas 10 is displayed on a user interface 24 defined above.

Notwithstanding the above described embodiments, in further possible embodiments the oral cavity, represented by the digital image(s) 1, may be segmented into a much higher number of unique surfaces than required by any of the above-mentioned dental frameworks. In possible embodiments the oral cavity can be segmented into 200-1000 uniquely identifiable surface regions, as illustrated e.g. in the 3D model in FIG. 8. These uniquely identifiable surface regions may represent a more granular surface identification, such as "the gum-attached lip-facing side of the bottom left incisor".

These uniquely identifiable surface regions can then be related to each other in different ways to form the above described regions (tooth surface regions 17, periodontal surface regions 18 and/or oral cavity regions 18), such as by aggregating in a dental surface identification framework (like a 5-surface model).

In possible embodiments, at least one of the statistical image segmentation algorithms 101, 102 uses neural networks (e.g. MaskRCNN, YOLO, CNN) based on annotations using an annotation type of at least one of boxes, polygons, or masks. During training of these statistical image segmentation algorithms, digital images from different angles of the same oral cavity may be obtained (including images taken in one sitting or over time). This makes it possible to calculate which surfaces are typically/statistically invisible on which particular images, which may further inform the statistical algorithm 103 trained to predict any invisible segments 6 based on visible segments 3.

In some embodiments, the statistical algorithm 103 trained to predict any invisible segments 6 based on visible segments 3 may be informed by the mapping of identified surfaces to predefined dental models, such as mapping onto a standard dental notation, e.g. a 5-surface tooth model or a 3-surface gum model.

The aforementioned statistical algorithms may further use a custom surface identification framework, such as clustering and/or distinguishing visually similar surfaces from each other, irrespectful of whether these are from a dental perspective non-related (or in the distinguishing case, that they are related). An example includes that the "chewing surface" of molars typically go under the surface type "occlusal" in most dental settings, but visually this surface has some quite distinguishable features/sub-surfaces that are used in algorithms.

In possible embodiments, the statistical object detection algorithm 104 uses a neural network model, more preferably a convolutional neural network (CNN) model, based on annotations using an annotation type of at least one of boxes, polygons, or masks. In an embodiment the statistical object detection algorithm 104 may use an R-CNN model (such as MaskRCNN).

In some embodiments, the method or system may detect contradictory input from different sources such as different digital images 1, non-image data 2, or data from a dental journal 27. Each data source in such cases is weighted statistically with regard to the amount of information it carries. For example, a very blurry image will often carry low information, and a high-quality image with clearly visible findings will carry more. Similarly, it will often carry more information that the person is experiencing severe pain (indicated via obtained non-image data 2), even though the digital images 1 may also show that they might have healthy gum tissue. In fact, a person's oral cavity will almost always show some degree of contradictory signs (e.g. strong enamel in some teeth, and progressed cavities in others or inflammation of the gums in the bottom part of the mouth, but non-inflamed in the top). Therefore, it is an integral part of the method and related system to handle and prioritize such contradictory signs.

The Oral Risk Atlas 10 may highlight such detected or determined contradictory input for a dental professional for further assessment and evaluation.

In possible embodiments, dental features 7 can be identified through a variety of different annotations, depending on the dental feature 7. Annotation types may include boundary boxes, polygons, focal points, and individual labelling of intelligently identified subset/local patches of the input image.

Some examples of dental features 7 related to indications of gum disease or inflammation:
- Swelling of gums/type of feature: form, contour, shape/,
- Redness of gums/type of feature: color, gradient, shade/,
- Gradient of redness/type of feature: color, gradient, shade/,
- Bleeding gums,
- Discolorations of teeth (due to lacking oral hygiene)/type of feature: color, gradient, shade/,
- External matter on teeth (due to lacking oral hygiene)/type of feature: texture, surface, roughness/,
- Presence of plaque,
- Exposure of root/type of feature: (primarily) color, gradient, shade,
- Recession of gums/type of feature: form, contour, shape/, and
- Cliff separating enamel and dental/type of feature: Form, contour, shape/.

Figure 3:
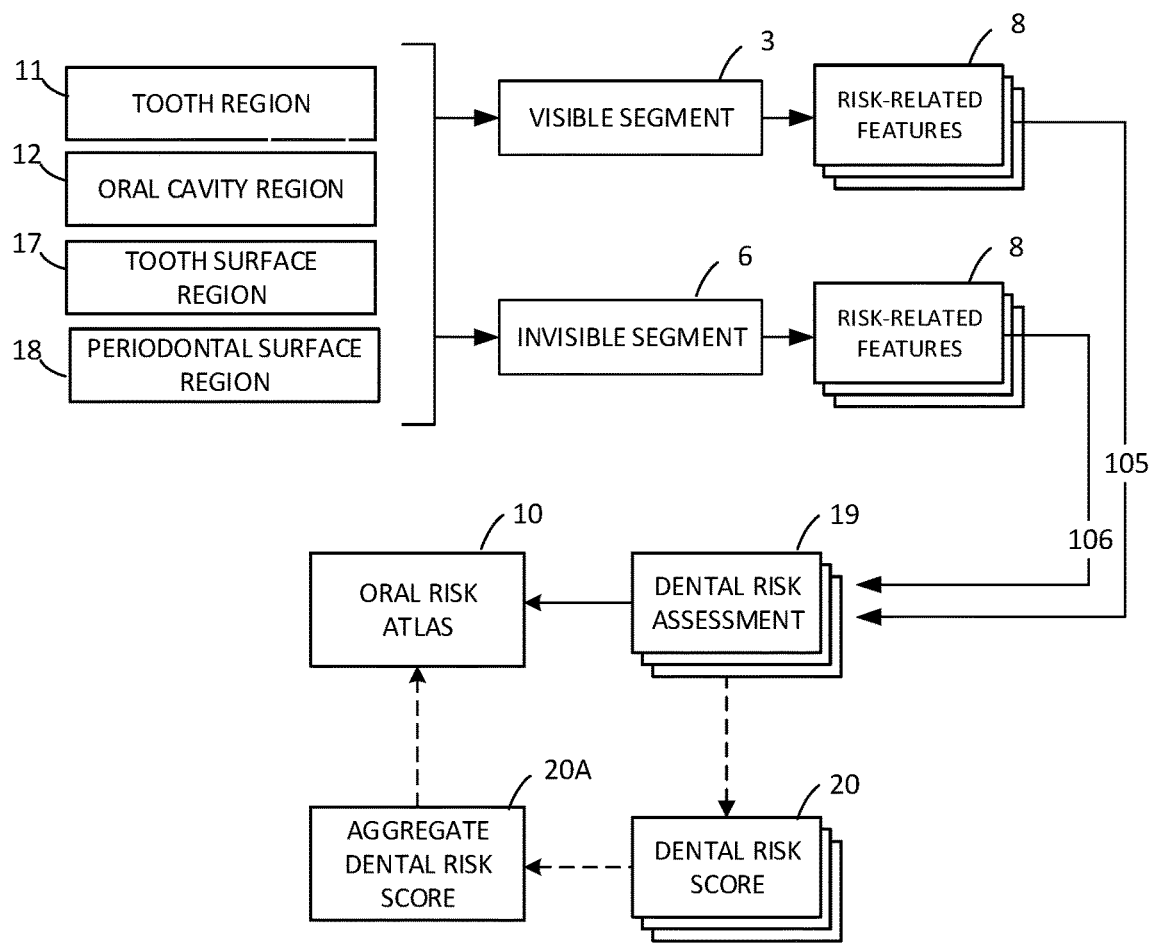
FIG. 3 shows a flow diagram of determining a dental risk assessment in accordance with a further implementation form of the first aspect.

FIG. 3 shows a flow diagram of determining dental risk assessments in accordance with the present disclosure, whereby features that are the same or similar to corresponding features previously described or shown herein are denoted by the same reference numeral as previously used for simplicity.

In particular, according to this embodiment the method further comprises determining dental risk assessments 19 for each tooth region 11, oral cavity region 12, tooth surface region 17 and periodontal surface region 18 associated with an identified visible segment 3 using a statistical risk assessment algorithm 105 trained to predict dental risk assessments 19 based on risk-related dental features 8 determined from the respective visible segments 3.

On the other hand, the method according to this embodiment also comprises determining a dental risk assessment 19 for each tooth region 11, oral cavity region 12, tooth surface region 17 and periodontal surface region 18 associated with a predicted invisible segment 6 using a statistical risk prediction algorithm 106 trained to predict dental risk assessments 19 based on risk-related dental features 8 determined from visible segments 3 adjacent to a respective invisible segment 6.

Once the dental risk assessments 19 are determined they are mapped to the Oral Risk Atlas 10 in a similar manner as described above with respect to the risk-related dental features 9.

Herein, a "dental risk assessment" preferably refers to an assessment determined based on a distillation or aggregation of risk-related features 8 in order to determine a person's oral health condition with respect to related risks and optionally treatment costs related to decreasing or eliminating these conditions and their related risks. For example, a dental risk assessment 19 may comprise at least one of identifying any oral health problems, diagnosing any oral health diseases, identifying any oral health risks, or determining that no symptoms of any oral health problems or diseases are present in a respective region of the oral cavity.

The person may have observed symptoms of an oral health problem or disease and may therefore wish to obtain digital images 1 of an area of his/her oral cavity to have his/her oral health assessed based on the images and additional non-image data 2. Or, the person may not have observed any symptoms but may, nevertheless, wish to have his/her oral health assessed. In an embodiment, this assessment may be part of a dental health treatment or follow-up plan prescribed by a dental professional, or an initial or follow-up assessment required by a health insurance provider, or specifically a dental insurance provider.

The dental risk assessment 19, whether performed locally or remotely, may comprise a distillation or aggregation of risk-related features 8 or derived risk scores in an easily comprehensible form for a patient, dental professional or insurance provider. Some examples for such distillations or aggregations to be presented: "5×3-sided and 3×1-sided fillings", "12 teeth of over 70% of risk of developing a cavity", or in case of an insurance provider: "there are 5 fillings, 3 of these are close to broken, the patient seems to further be developing level 2 cavities in a neighboring region—that means this patient would be in the Red Group for us".

In possible further embodiments the dental risk assessment 19 may include a diagnosis identifying a "medical finding" (which may refer to both normal and abnormal medical states), a referral to a dental professional, an estimate of the urgency of an oral health problem, a recommendation for self-treatment, etc. An abnormal medical state herein may refer to an oral disease or other oral health problem.

Further, herein, "oral health problem" or "oral disease" may refer to at least one of Abnormal taste in mouth, Abrasion of tooth, Acid reflux, Acute necrotizing ulcerative gingivitis, Addison's disease, Alveolitis of jaw, Amalgam tattoo, Amelogenesis imperfecta, Anemia, Aphthous ulcer of mouth, Atrophy of tongue papillae, Black hairy tongue, Bleeding gums, Broken tooth injury, Bruxism (teeth grinding), Burning mouth syndrome, Cancer, Candidiasis, Cheek biting, Cheilosis, Chemical burn (mouth), Chicken pox (Varicella), Cold sore, Complete avulsion of tooth, Contusion, Crazing of enamel, Cyst, Dental caries, Dental filling lost, Dental peri-implant mucositis, Dental plaque, Dental restoration present, Dentinogenesis imperfecta, Denture stomatitis, Diastema of teeth, Early tooth exfoliation, Electrical burn, Enamel hypoplasia, Enlarged labial frenulum, Erosion of teeth, Eruption cyst, Erythema, Erythroleukoplakia of internal part of mouth, Excessive salivation, Fibroma, Fistula, Fluorosis, Fordyce's disease, Fracture of tooth, Fractured dental restoration, Geographic tongue, Gingival recession, Gingivitis, Glossopyrosis, Hemangioma, Herpes labialis, Herpes zoster, Herpes infection, Hyperplasia of gingiva, Infectious mononucleosis, Leukemia, Leukoedema, Leukoplakia, Lichen planus (mouth), Linea alba of oral mucosa, Lip biting, Lipoma, Lymphadenopathy, Malignant melanoma, Malignant tumor of major salivary gland, Malocclusion of teeth, Measles, Melanin pigmentation (mouth), Melanocytic nevus (mouth), Melanoma in situ (mouth), Mucocele of mouth, Mumps, Necrosis of the pulp, Osteoporosis, Pain in throat, Papillary hyperplasia, Papilloma, Parulis, Pemphigoid, Pemphigus, Pericoronitis, Periodontal abscess, Periodontitis, Pseudomembranous thrush, Pulpitis, Pyogenic granuloma, Rubella, Sexually transmitted infectious disease, Sialolithiasis, Sinusitis, Smokeless tobacco keratoses, Smoker's melanosis, Staining of tooth, Stomatitis, Subluxation of tooth, Syphilis, Teething syndrome, Temporomandibular joint disorder, Thermal burn, Tongue biting, Tonsillitis, Tooth absent, Tooth sensitivity to brush or floss, Tooth sensitivity to cold, Tooth sensitivity to palpation, Traumatic granuloma, Traumatic injury, Trigeminal neuralgia, Turner's Tooth, Ulcer, Verrucous carcinoma, Vitamin deficiency, Wegener's granulomatosis, White sponge nevus of mucosa, or Xerostomia. Further, herein, "oral health" or "oral health sign" may refer to at least one of Healthy gums, Healthy enamel, Healthy mucosa, Healthy tongue, Healthy lips, Healthy Roof of Mouth, Healthy Saliva Gland, or the absence of any oral health problem.

Particularly, the dental risk assessment 19 may comprise information mapped to an Oral Risk Atlas 10 and indicating whether the person is a candidate for an oral treatment, based on the images 1 and non-image data 2, and informing the person, preferably via a user interface 24, whether he/she is a candidate for an oral treatment.

In an embodiment, determining the dental risk assessment 19 comprises calculating a dental risk score 20 for each tooth region 11, oral cavity region 12, tooth surface region 17 and periodontal surface region 18. The dental risk score 20 may be determined e.g. as a percentage value ranging from 1 to 100% or a discrete value ranging from 1 to 5.

The dental risk scores 20 may indicate a risk of a possible action needed (e.g. risk of needing a crown) and/or an urgency level (high, medium, low) of a dental risk.

In an embodiment mapping of dental risk scores 20 to the Oral Risk Atlas 10 is further used by an insurance provider for calculating an insurance package.

Once the dental risk scores 20 are calculated they may be mapped, similarly as described above, to the Oral Risk Atlas 10, either in a text format, or by visualizing each percentage value or discrete value in the Oral Risk Atlas 10 using a predefined color scheme, such as assigning a red color to the highest risk levels, orange color to medium risk levels, and a white color to low risk levels, while indicating nonexistent or non-defined risk levels with black.

In a further possible embodiment, the method may further comprise calculating an aggregate dental risk score 20A based on aggregating the dental risk scores 20 for each tooth region 11, oral cavity region 12, tooth surface region 17 and periodontal surface region 18, and displaying the aggregate dental risk score 20A as part of the Oral Risk Atlas 10.

In possible embodiments, at least one of the statistical risk assessment algorithm 105 or the statistical risk prediction algorithm 106 further uses static syntax analysis implemented as an iteration over a number of tooth surface regions 17 impacted by a dental feature 7 (such as a filling), each tooth surface region 17 contributing to a higher dental risk score 20. At least one of the statistical risk assessment algorithm 105 or the statistical risk prediction algorithm 106 may further use predefined conditions on compound contributions to the determined dental risk score 20.

In possible embodiments, at least one of the statistical risk assessment algorithm 105 or the statistical risk prediction algorithm 106 is based on a Support Vector machine model and/or uses at least one of a classical linear regression model, an ordinal-data-based statistical algorithm, or neural networks supplemented with syntax analyses of predefined conditions (e.g. a tooth surface is on a tooth, not on the gums), optionally further supplemented by manual input from a dental professional or querying a dental knowledge database.

In possible embodiments, at least one of the statistical risk assessment algorithm 105 or the statistical risk prediction algorithm 106 is further supplemented with syntax analyses aggregating risks of specific treatments with a cost of each treatment type for calculating the dental risk scores 20 and the aggregate dental risk score 20A.

The algorithms for risk score calculation may further take into account at least one of:
- risks of future expenses;
- risk of negative progression in a given disorder (e.g. from level 3 periodontitis to level 4);
- risk of chronic effects, e.g. going from reversible gingivitis to irreversible recession of the gums due to gingivitis.

Figure 4:
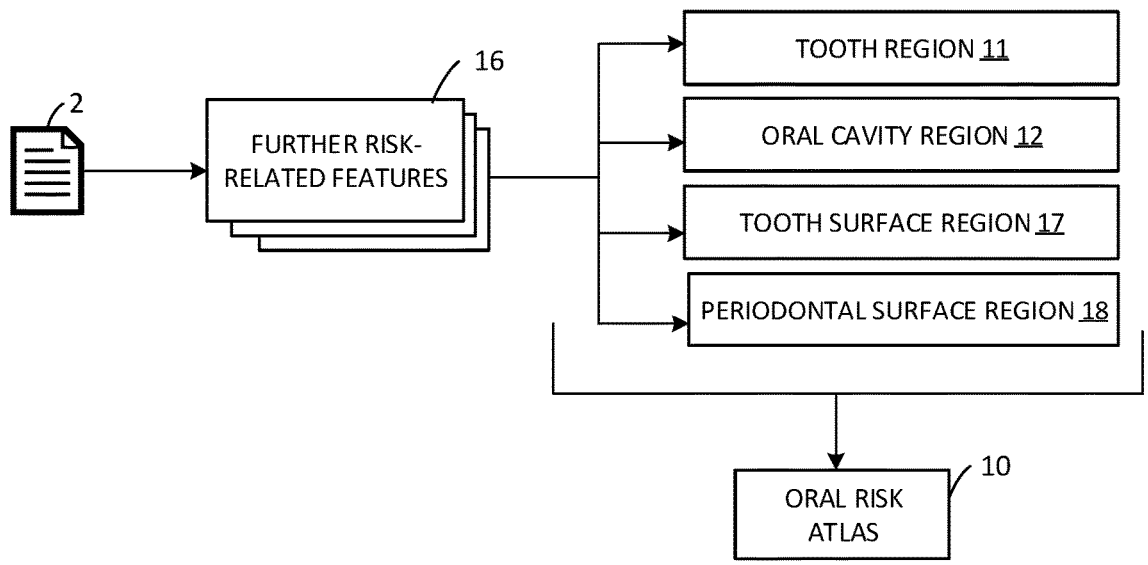
FIG. 4 shows a flow diagram of processing non-image data to extract further risk-related dental features in accordance with a possible implementation form of the first aspect.

In an embodiment as illustrated in FIG. 4, the non-image data 2 obtained from the person (e.g. in the form of responses to a sequence of questions presented in a chat dialogue) is processed to extract further risk-related dental features 16 linked to any one of the tooth region 11, oral cavity region 12, tooth surface region 17 or periodontal surface region 18. After the further risk-related dental features 16 are extracted, they are mapped, similarly to the risk-related dental features 8 described above, to their respective regions according to the predefined dental surface identification framework, predefined dental notation framework, or predefined oral cavity surface identification framework, for generating the Oral Risk Atlas 10.

In an embodiment the non-image data 2 is processed using a syntax analysis algorithm to extract a structured database of non-image signals. The extracted non-image signals may comprise at least one of "Sharp", "Pulsatile", "Burning sensation", "Itching", "Tingling", "Radiating", "Stabbing", "Penetrating", "Acute", "Spontaneous", "Periodic", "Constantly", "Provoked", "Swelling", "Growth of tissue", "Abnormal taste", "Bad breath", "Irregular surface", "Pedunculated", "Redness", "Bleeding spot", "Firm", "Soft", "Compressible", "Pain when biting", "Plaque", "Pain when swallowing", "Sore throat", "Sore gums", "Bleeding gums", "Recession of the gums", "Touch sensitive", or "Loose tooth".

In further possible embodiments, the extracted non-image signals may indicate at least one of:
- symptoms or signs of health regarding intraoral colors, surface structures, contours, wounds, texture, general health, taste in mouth, breath, saliva, healing process, pain;
- symptom triggers related to touch or icing, biting down, movement of tongue or jaw; or
- behavioral data regarding oral habits, general health, medicine intake, comorbidities of periodontitis, history of trauma, history of oral procedures, pregnancy, or tobacco usage.

Figure 5:
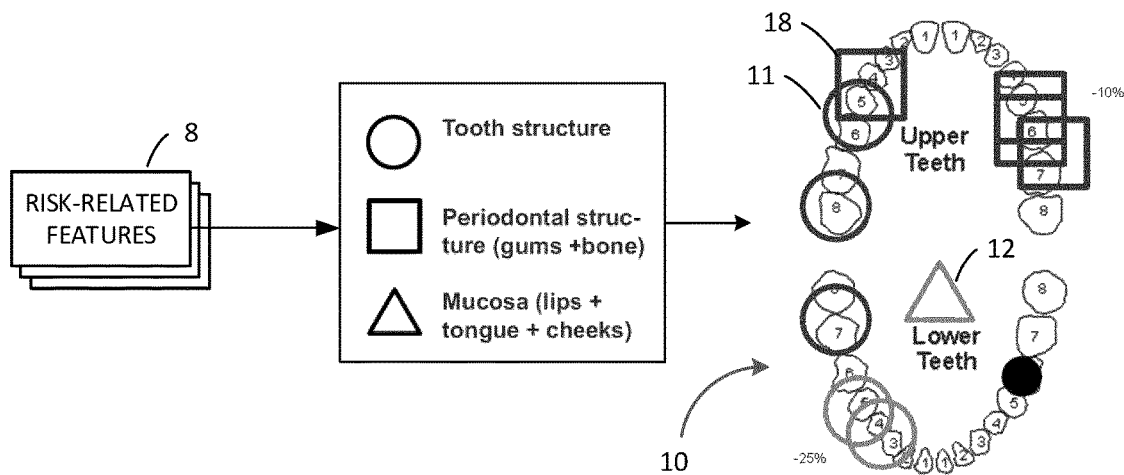
FIG. 5 shows mapping risk-related dental features to an Oral Risk Atlas in accordance with a possible implementation form of the first aspect.

FIG. 5 shows a possible embodiment of the Oral Risk Atlas 10, wherein the risk-related dental features 8 are mapped to different tooth regions 11, oral cavity regions 12 and periodontal surface regions 18 according to a dental notation framework, using a predefined geometrical shape for each different region—in this exemplary embodiment, a circle for tooth regions 11, a rectangle for periodontal surface regions 18 and a triangle for oral cavity regions 12.

The dental notation framework may be a dental map with a standardized tooth numbering system as described above and may use the same 2D oral cavity model for every person, or a customized 2D oral cavity model encapsulating individual deviations from a standard model (but still using standardized numbering for easier comprehensibility). The customized 2D oral cavity model may be determined based on input from a specific person such as digital image(s) 1 and non-image data 2 relating to the person's oral cavity, and/or additional non-image data 2 extracted from a dental journal 27 or dental medical history of the person. In further possible embodiments the 2D oral cavity model may be based on a modeling of the specific person's oral cavity using known oral cavity modeling techniques such as 2D or 3D digital modeling using direct mapping (such as laser mapping) or indirect mapping (such as orthodontic molds).

Figure 6:
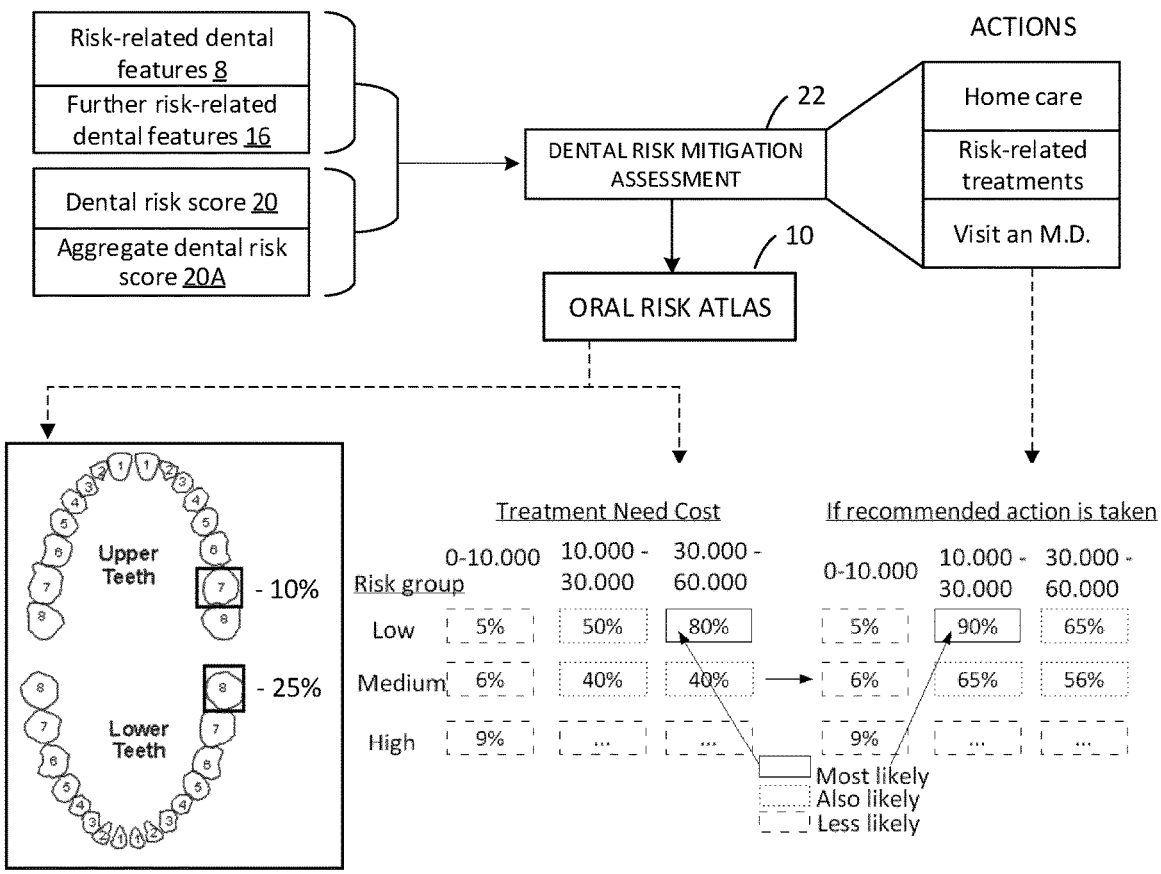
FIG. 6 shows a flow diagram of determining dental risk mitigation assessments in accordance with a possible implementation form of the first aspect.

FIG. 6 shows a flow diagram of determining dental risk mitigation assessments in accordance with the present disclosure, whereby features that are the same or similar to corresponding features previously described or shown herein are denoted by the same reference numeral as previously used for simplicity.

In particular, according to the method of this embodiment certain dental risk mitigation assessments 22 are determined based on previously determined risk-related dental features 8, further risk-related dental features 16, dental risk scores 20 and/or an aggregate dental risk score 20A. In an embodiment dental history of a person is further taken into account for determining dental risk mitigation assessments 22, based on either the provided non-image data 2 or extracted data from a dental journal 27 (e.g. average lifetime of previous crowns).

The dental risk mitigation assessment 22 may comprise a Dental Risk Mitigation Score across a predefined set of possible actions to take for the person, the possible actions comprising for example: home care actions related to following a dental routine or customized dental plan such as more frequent flossing, mouth rinse; risk-related specific treatments (e.g. "a crown is made today"); or prompts to visit a dental professional. The dental risk mitigation assessments 22 may then be presented to a person via a user interface 24 either in a text format, or in a visual interpretation.

In other words, dental risk mitigation assessments 22 may represent the likelihood or plausibility of mitigating a risk of a defined oral health issue given a defined action or a set of defined actions.

In a preferred embodiment, generating the Oral Risk Atlas 10 further comprises mapping potential gains of the possible actions to the Oral Risk Atlas 10, such as a decrease of a dental risk score 20 or aggregate dental risk score 20A, or a decrease of likely treatment costs, as illustrated in FIG. 6.

Figure 7:
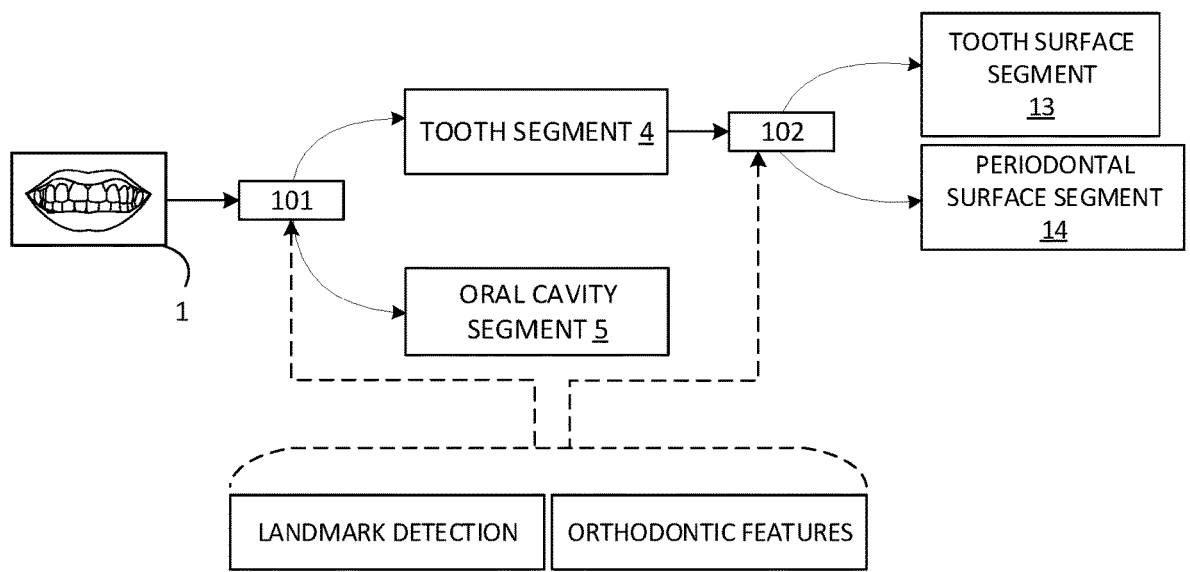
FIG. 7 shows a flow diagram of segmentation of a digital image using statistical image segmentation algorithms in accordance with a possible implementation form of the first aspect.

FIG. 7 shows a flow diagram of segmentation of a digital image 1 using statistical image segmentation algorithms in accordance with the present disclosure, whereby features that are the same or similar to corresponding features previously described or shown herein are denoted by the same reference numeral as previously used for simplicity.

As described above in detail, the at least one digital image 1 of the person's oral cavity may first be segmented, using a first statistical image segmentation algorithm 101, into tooth segments 4 and oral cavity segments 5, wherein each tooth segment 4 relates to a distinct tooth and its related area within the oral cavity and each oral cavity segment 5 relates to a distinct non-tooth-related area within the oral cavity. The tooth segments 4 may then be further segmented, using a second statistical image segmentation algorithm 102, into tooth surface segments 13 and periodontal surface segments 14, each tooth surface segment 13 relating to a distinct surface of a distinct tooth within the oral cavity and each periodontal surface segment 14 relating to a structure surrounding or supporting a distinct tooth within the oral cavity.

In a possible embodiment, segmentation into tooth surface segments 13 and periodontal surface segments 14 can be based on the digital image 1 as input for the second statistical image segmentation algorithm 102.

In a preferred embodiment, at least one of the first statistical image segmentation algorithm 101 or second statistical image segmentation algorithm 102 further uses landmark detection based on landmarks or focal points, supplemented with spatial or vector analyses of orthodontic features, such as the orientation of each tooth and the relation between adjacent and other teeth in the oral cavity.

Figure 8:
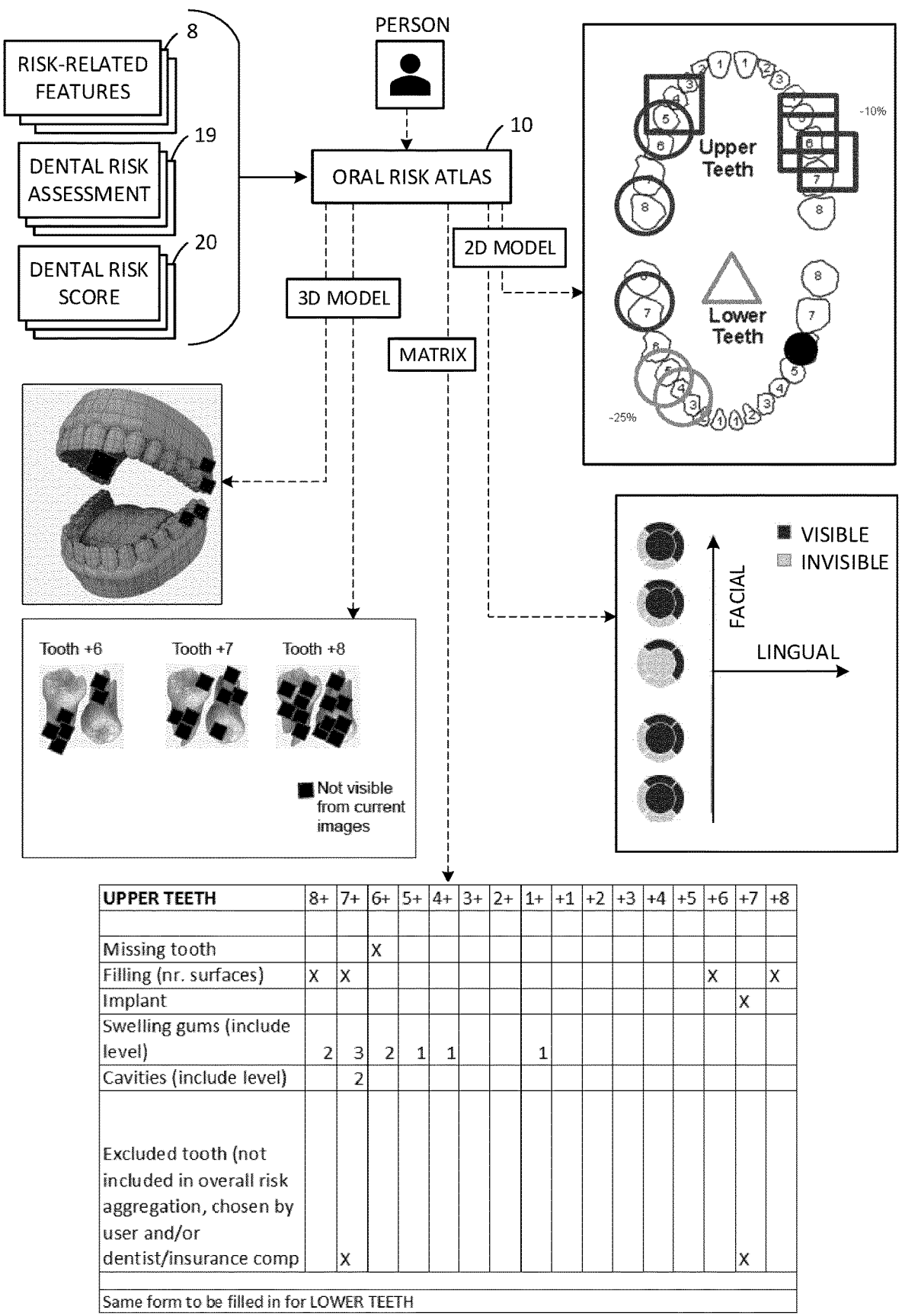
FIG. 8 illustrates different options for generating an Oral Risk Atlas in accordance with possible implementation forms of the first aspect.

FIG. 8 illustrates different options for mapping and displaying an Oral Risk Atlas 10 in accordance with the present disclosure, whereby features that are the same or similar to corresponding features previously described or shown herein are denoted by the same reference numeral as previously used for simplicity.

As shown in the figure, the Oral Risk Atlas 10 may be presented as a matrix chart, whereby risk-related dental features 8 and/or dental risk assessments 19 (listed in separate rows) are mapped to respective teeth regions 11 (listed in separate columns). In an embodiment as illustrated in the figure, the regions of the upper teeth and lower teeth are mapped in separate charts, whereby the +/− prefix of each teeth numbering indicates upper or lower teeth. In the charts, risk-related dental features 8 and/or dental risk assessments 19 may be marked by a binary indicator such as an "X" indicating presence or non-presence (e.g. root canal or plaque) or as a discrete value that may range from e.g. 1 to 5 indicating the number of tooth surfaces that are affected by a filling, or stages of development of a tooth cavity. Further possible indicators may include e.g. abbreviations (AU,MK,IM,HK) indicating the presence of different types of dental posts or crowns on a tooth, and detected condition of a dental ligament (indicator determined based on a dental poche larger than a predefined size, e.g. 5 mm). In addition to dental features 8 and/or dental risk assessments 19, the charts may indicate presence or exclusion of a whole tooth from the Oral Risk Atlas 10 based on the digital image(s) 1 or non-image data 2 provided by the person.

According to another embodiment illustrated in the figure, the Oral Risk Atlas 10 may be presented as a 2D oral cavity model, whereby risk-related dental features 8 and/or dental risk assessments 19 are mapped to respective tooth regions 11 according to a dental notation framework as described before. As also described before, the dental notation framework may use the same 2D oral cavity model for every person, or a customized 2D oral cavity model based on input from a specific person such as digital image(s) 1 and non-image data 2 relating to the person's oral cavity, and/or additional non-image data 2 extracted from a dental journal 27 or dental medical history of the person. In further possible embodiments the 2D oral cavity model may be based on a modeling of the specific person's oral cavity using known oral cavity modeling techniques such as 3D digital modeling using direct mapping (such as laser mapping) or indirect mapping (such as orthodontic molds).

According to another embodiment illustrated in the figure, the Oral Risk Atlas 10 may be presented as a 2D tooth surface model, whereby risk-related dental features 8 and/or dental risk assessments 19 are mapped to respective tooth surface regions 17 according to a dental surface identification framework as described before.

According to another embodiment illustrated in the figure, the Oral Risk Atlas 10 may be presented as a 3D oral cavity model, whereby risk-related dental features 8 and/or dental risk assessments 19 are mapped to respective tooth regions 11 on a 3D dental model. Similarly to the 2D oral cavity model described above, the 3D oral cavity model may be the same 3D oral cavity model for every person, or a customized 3D oral cavity model based on input from a specific person such as digital image(s) 1 and non-image data 2 relating to the person's oral cavity, and/or additional non-image data 2 extracted from a dental journal 27 or dental medical history of the person (including e.g. X-rays). In further possible embodiments the 3D oral cavity model may be based on a modeling of the specific person's oral cavity using known oral cavity modeling techniques such as 3D digital modeling using direct mapping (such as laser mapping) or indirect mapping (such as orthodontic molds).

In particular, such a 3D oral cavity model may offer more granularity regarding individual surfaces for feature mapping.

In an embodiment as illustrated in the figure, risk-related dental features 8 and/or dental risk assessments 19 may be mapped to individual 3D teeth models according to a predefined dental surface identification framework, including a visibility of the root region of each teeth.

In an embodiment also illustrated in the figure, risk-related dental features 8 and/or dental risk assessments 19 linked to invisible surface segments 15 may be marked on the 3D models to indicate that these features and/or assessments are based on regions not visible on the input digital image(s) 1, or in some cases to indicate probability of detected features and assessment using a percentage value (such as "7% probability of composite filling" or "89% probability of gold filling").

In possible embodiments, risk-related dental features 8 and/or dental risk assessments 19 can be automatically or manually filtered or altered (e.g. by a dental professional) before mapping onto the Oral Risk Atlas, wherein the filtering or altering may be based on sensitivity of information (e.g. possible risk of oral cancer may cause unnecessary discomfort or panic which should be subject for further evaluation by a dental professional) or comprehensibility of presented terms (e.g. different phrases used for different end users such as dental professionals, insurance professionals, or standard patients).

FIG. 9 illustrates a computer-based system for assessing oral health of a person in accordance with the present disclosure.

A client device 26 is provided, as part of the computer-based system, comprising at least one digital camera 23 configured to capture digital images and means such as an input device 28 for obtaining further non-image input. The client device 26 may be a portable computing device. In the embodiment illustrated in FIG. 9, the client device 26 is a smartphone that may comprise both a front camera above the display and a main camera on the rear side. In another embodiment, the client device 26 may be e.g. a tablet computer (tablet) with corresponding features (display and camera).

In an embodiment, the client device 26 may be configured to execute a software application ("app") and comprises a digital camera 23 for capturing images and a display for displaying the images as part of a user interface 24, wherein the display and the digital camera 23 may be provided on opposite sides of the housing of the client device 26. In another embodiment, the digital camera 23 for capturing images may be a secondary camera provided on the same side of the housing of the mobile device as the display. In an embodiment the display may comprise a touch screen that functions as the input device 28 and provides means for obtaining non-image data 2 from a person by user interaction with the help of a user interface 24.

The client device 26 may further comprise an integrated or external communications interface for connecting to other client devices directly or indirectly via a computer network. For example, the communications interface can include Wi-Fi enabling circuitry that permits wireless communication according to one of the 802.11 standards or a private network. Other wired or wireless protocol standards, such as Bluetooth, can be used in addition or instead.

The client device 26 may further comprise an internal bus arranged to provide a data transfer path for transferring data to, from, or between the mentioned components of the client device 26.

FIG. 9 further illustrates a wireless system in accordance with the present disclosure, wherein the client device 26 may communicatively be connected to a network of computer nodes using an integrated or external communications interface, for transmitting image data and/or non-image data from the client device 26 to a server device 25 and/or for receiving data from a server device 25. The figure shows a diagrammatic representation of an exemplary wireless network, such as a cellular telephone network, the internet, or a cloud-based network, comprising the client device 26 and a server device 25 that can be e.g. a dental professional's workstation. Image data 1 and/or non-image data 2 may be transmitted from the client device 26 to the server device 25 for remote assessment, processing, and/or storage of the data. The transmission of data may be synchronous, asynchronous, or a mixture of synchronous and asynchronous data transmission.

As also illustrated in FIG. 9, a risk database 9 may also be implemented as part of the computer-based system to define logical relationships between dental features 7 and their related oral health risks. The risk database 9 may be stored on a computer-readable storage medium of the server device 25, or on a computer-readable storage medium of the client device 26, or even on a computer-readable storage medium of a separate entity (e.g. a cloud-based storage provider) that is in data connection with at least one of the server device 25 or the client device 26 and can be called by a dental risk analysis application running on the server device 25 or the client device 26.

The method described above for assessing oral health may at least partly be implemented as a computer program product encoded on a computer-readable storage medium of a computer-based device, such as a server device 25 or client device 26 described above. The computer program product may in effect be realized in the form of a dental risk analysis application which may be executed by one or more processors which may load the application software on a memory of a computer-based device, such as the server device 25 or client device 26 described above.

The various aspects and implementations have been described in conjunction with various embodiments herein. However, other variations to the disclosed embodiments can be understood and effected by those skilled in the art in practicing the claimed subject-matter, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems.

The reference signs used in the claims shall not be construed as limiting the scope.

The invention claimed is:

1. A computer program embodied on a non-transitory computer-readable medium and comprising instructions which, when the program is executed by a computer, cause the computer to:

obtain at least one digital image (1) of a person's oral cavity;

obtain non-image data (2) associated with the person, the non-image data (2) comprising anamnestic information about the person;

process the at least one digital image (1) or a representation thereof using a first statistical image segmentation algorithm (101) trained to identify at least one visible segment (3), the at least one visible segment (3) being one of a tooth segment (4) or an oral cavity segment (5), wherein each tooth segment (4) relates to a distinct tooth and its related area within the oral cavity and each oral cavity segment (5) relates to a distinct non-tooth-related area within the oral cavity;

process the at least one visible segment (3) using a statistical algorithm (103) trained to predict at least one invisible segment (6) based on at least one visible segment (3), each of the at least one invisible segment (6) relating to an area within the oral cavity that is not visible on any of the at least one digital image (1); and process the at least one visible segment (3) and the at least one invisible segment (6) using a statistical object detection algorithm (104) trained to identify dental features (7) linked to at least one visible segment (3) and at least one invisible segment (6), wherein the statistical object detection algorithm (104) uses the non-image data (2) as input regarding what dental features (7) to look for.

2. The computer program according to claim 1, comprising further instructions which, when the program is executed by a computer, cause the computer to:

select risk-related dental features (8) from the identified dental features (7) using a risk database (9) that defines logical relationships between identified dental features (7) and their related oral health risks;

generate an Oral Risk Atlas (10) by mapping risk-related dental features (8) linked to any tooth segment (4) to a respective tooth region (11) according to a predefined dental notation framework, mapping risk-related dental features (8) linked to any oral cavity segment (5) to a respective oral cavity region (12) according to a predefined oral cavity surface identification framework, and mapping risk-related dental features (8) linked to any invisible segment (6) to a respective tooth region (11) or oral cavity region (12) according to the predefined dental notation framework and the oral cavity surface identification framework; and display the Oral Risk Atlas (10) on a user interface (24).

3. The computer program according to claim 2, comprising further instructions which, when the program is executed by a computer, cause the computer to:

process at least one tooth segment (4) of the at least one visible segment (3) using a second statistical image segmentation algorithm (102) trained to identify at least one tooth surface segment (13) and at least one periodontal surface segment (14), each tooth surface segment (13) relating to a distinct surface of a distinct tooth within the oral cavity and each periodontal surface segment (14) relating to a structure surrounding or supporting a distinct tooth within the oral cavity;

process the at least one tooth surface segment (13) and at least one periodontal surface segment (14) using a statistical algorithm (103) trained to predict any invisible surface segments (15), each invisible surface segment (15) relating to a distinct surface of a distinct tooth or a structure surrounding or supporting a distinct tooth within the oral cavity that is not visible on any of the at least one digital image (1);

identify dental features (7) linked to any of the at least one tooth surface segment (13), at least one periodontal surface segment (14), and invisible surface segments (15) by processing the at least one tooth surface segment (13), the at least one periodontal surface segment (14) and invisible surface segment (15) using the statistical object detection algorithm (104); and select risk-related dental features (8) linked to any of the at least one tooth surface segment (13), at least one periodontal surface segment (14), and invisible surface segments (15) from the identified dental features (7) using the risk database (9);

wherein generating the Oral Risk Atlas (10) further comprises:

mapping the risk-related dental features (8) linked to the at least one the tooth surface segments (13) to a respective tooth surface region (17) according to a predefined dental surface identification framework, mapping the risk-related dental features (8) linked to the at least one periodontal surface segments (14) to a respective periodontal surface region (18) according to a predefined dental surface identification framework, and mapping the risk-related dental features (8) linked to the invisible surface segments (15) to a respective tooth surface region (17) or periodontal surface region (18) according to the predefined dental surface identification framework.

4. The computer program according to claim 3, comprising further instructions which, when the program is executed by a computer, cause the computer to:

determine a dental risk assessment (19) for each tooth region (11), oral cavity region (12), tooth surface region (17) and periodontal surface region (18) associated with an identified visible segment (3) using a statistical risk assessment algorithm (105) trained to predict dental risk assessments (19) based on risk-related dental features (8) determined from respective visible segments (3); wherein generating the Oral Risk Atlas (10) further comprises mapping the dental risk assessment (19) to the Oral Risk Atlas (10).

5. The computer program according to claim 3, comprising further instructions which, when the program is executed by a computer, cause the computer to:

determine a dental risk assessment (19) for each tooth region (11), oral cavity region (12), tooth surface region (17) and periodontal surface region (18) associated with a predicted invisible segment (6) using a statistical risk prediction algorithm (106) trained to predict dental risk assessments (19) based on risk-related dental features (8) determined from visible segments (3) adjacent to a respective invisible segment (6);

wherein generating the Oral Risk Atlas (10) further comprises mapping the dental risk assessments (19) to the Oral Risk Atlas (10).

6. The computer program according to claim 3, comprising further instructions which, when the program is executed by a computer, cause the computer to:

determine a dental risk assessment (19) by calculating a dental risk score (20) for each tooth region (11), oral cavity region (12), tooth surface region (17) and periodontal surface region (18) as a percentage value (ranging from 1 to 100%) or a discrete value (ranging from 1 to 5);

wherein generating the Oral Risk Atlas (10) further comprises mapping the dental risk scores (20) to the Oral Risk Atlas (10).

7. The computer program according to claim 6, comprising further instructions which, when the program is executed by a computer, cause the computer to:
calculate an aggregate dental risk score (20A) based on aggregating the dental risk scores (20) for each tooth region (11), oral cavity region (12), a tooth surface region (17) and a periodontal surface region (18).

8. The computer program according to claim 2, comprising further instructions which, when the program is executed by a computer, cause the computer to:
process the non-image data (2) to extract further risk-related dental features (16) linked to any one of the tooth region (11), oral cavity region (12), tooth surface region (17) or periodontal surface region (18);
wherein generating the Oral Risk Atlas (10) further comprises mapping the further risk-related dental features (16) to the respective regions.

9. The computer program according to claim 2, comprising further instructions which, when the program is executed by a computer, cause the computer to:
determine dental risk mitigation assessments (22) comprising possible actions to take for the person based on the risk-related dental features (8), the possible actions comprising at least one of
  home care actions related to following a dental routine or customized dental plan, such as prompts for more frequent flossing,
  risk-related treatments, or
  prompts to visit a dental professional;
wherein generating the Oral Risk Atlas (10) further comprises mapping potential gains of the possible actions to the Oral Risk Atlas (10).

10. The computer program according to claim 2, comprising further instructions which, when the program is executed by a computer, cause the computer to at least one of:
map the risk-related dental features (8) to respective regions using a matrix scheme; or
map the risk-related dental features (8) to respective regions based on a 2D or 3D oral cavity model, the oral cavity model being generated using a standardized dental model or a dental model of the person.

11. The computer program according to claim 2, wherein the digital image (1) is at least one of an intraoral or extraoral high resolution color photograph, obtained through a dental risk analysis application by prompting the person to take a photograph with a digital camera (23) of a client device (26) of one or more areas of the oral cavity of the person.

12. The computer program according to claim 2, wherein the non-image data (2) is obtained, in the form of at least one of a text input, spoken input or input by selection of selecting at least one of several presented answers, through a dental risk analysis application by performing a dialogue with the person through a user interface (24) of a client device (26).

13. The computer program according to claim 2, comprising further instructions which, when the program is executed by a computer, cause the computer to:
obtain additional non-image data (2) by extracting from a dental journal (27) or dental medical history of the person.

14. A computer-based system comprising:
a digital camera (23) configured to obtain a digital image (1) of an oral cavity (31) of a person;
an input device (28) configured to obtain non-image data (2) associated with the person, the non-image data (2) comprising anamnestic information about the person;
a computer-readable storage medium comprising a computer program according to claim 2; and
one or more processors operable to execute the computer program; and
a user interface (24) configured to display an Oral Risk Atlas (10) generated by the computer program.

15. A computer-based system according to claim 14, the system comprising:
a client device (26) comprising at least the digital camera (23), the input device (28) and the user interface (24); and
a server device (25) in data connection with the client device (26), the server device comprising at least the computer-readable storage medium and the one or more processors.

* * * * *